United States Patent [19]

Proctor

[11] Patent Number: 5,723,502
[45] Date of Patent: Mar. 3, 1998

[54] TOPICAL SPIN TRAP COMPOSITION AND METHOD

[76] Inventor: Peter H. Proctor, 4126 Southwest Freeway, Ste. 1616, Houston, Tex. 77027

[21] Appl. No.: 465,411

[22] Filed: Jun. 5, 1995

Related U.S. Application Data

[63] Continuation-in-part of Ser. No. 229,374, Apr. 18, 1994, Pat. No. 5,470,876, and Ser. No. 193,228, Feb. 7, 1994, Pat. No. 5,472,687, each is a continuation-in-part of Ser. No.21,970, Feb. 24, 1993, Pat. No. 5,352,442, which is a continuation-in-part of Ser. No. 149,720, Jan. 29, 1988, abandoned, which is a continuation-in-part of Ser. No. 8,186, Jan. 28, 1987, abandoned, which is a continuation-in-part of Ser. No. 858,050, Apr. 30, 1986, abandoned, which is a continuation-in-part of Ser. No. 757,131, Jul. 18, 1985, abandoned.

[51] Int. Cl.$^6$ .................. A61K 31/04; A61K 31/40; A61K 31/44
[52] U.S. Cl. .................. 514/741; 514/740; 514/424; 514/357
[58] Field of Search .................. 514/424, 644, 514/645, 741, 740, 352; 568/949, 939; 564/300

[56] References Cited

U.S. PATENT DOCUMENTS

| | | | |
|---|---|---|---|
| Re. 35,112 | 12/1995 | Carney et al. | 514/400 |
| 2,409,754 | 10/1946 | Henze | 548/301 |
| 2,986,573 | 5/1961 | Topliss | 514/223.2 |
| 3,257,390 | 6/1966 | Patchett | 540/41 |
| 3,461,461 | 8/1969 | Anthony et al. | 544/323 |
| 3,527,864 | 9/1970 | MacMillen et al. | 425/59 |
| 3,551,554 | 12/1970 | Herschler | 424/7.1 |
| 3,834,073 | 9/1974 | Dorschner et al. | 514/644 |
| 3,896,238 | 7/1975 | Smith | 514/777 |
| 4,139,619 | 2/1979 | Chidsey, III | 424/45 |
| 4,153,722 | 5/1979 | Campbell et al. | 564/265 |
| 4,189,039 | 2/1980 | Soldati | 544/12 |
| 4,254,145 | 3/1981 | Birnbaum | 424/305 |
| 4,344,941 | 8/1982 | Weichert | 424/243 |
| 4,347,245 | 8/1982 | Shapiro | 424/241 |
| 4,367,227 | 1/1983 | Bingham | 514/178 |
| 4,444,762 | 4/1984 | Rajadhyaksha | 424/180 |
| 4,456,600 | 6/1984 | Wiechert | 424/238 |
| 4,596,812 | 6/1986 | Chidsey, III | 424/251 |
| 4,866,067 | 9/1989 | Di Schiena | 514/275 |
| 5,036,097 | 7/1991 | Floyd et al. | 514/400 |
| 5,120,831 | 6/1992 | Pickart | 530/331 |
| 5,177,061 | 1/1993 | Pickart | 514/18 |
| 5,214,032 | 5/1993 | Pickart | 514/16 |
| 5,252,559 | 10/1993 | Kronholm | 514/18 |
| 5,256,678 | 10/1993 | Nakaguchi | 514/346 |
| 5,455,272 | 10/1995 | Janzen et al. | 514/579 |
| 5,475,032 | 12/1995 | Carney | 514/526 |
| 5,569,663 | 10/1996 | Ribier et al. | 514/315 |

FOREIGN PATENT DOCUMENTS

| | | |
|---|---|---|
| 0027655 | 4/1981 | European Pat. Off. . |
| 0249397 | 12/1987 | European Pat. Off. . |
| 0273202 | 7/1988 | European Pat. Off. . |
| 0327263 | 8/1989 | European Pat. Off. . |
| 0415598 | 3/1991 | European Pat. Off. . |
| 8022644 | 1/1996 | Japan . |
| 2198132 | 6/1988 | United Kingdom . |
| 8302558 | 8/1983 | WIPO . |
| 8600616 | 1/1986 | WIPO . |
| 8700427 | 1/1987 | WIPO . |
| 9304669 | 3/1993 | WIPO . |

OTHER PUBLICATIONS

Thornalley, P.J. et al., "The Effect of Nitrone spin trapping agents on red cell glucose metabolism", CA 105:92581 (1986).

Carney et al., "Spin trapping agents for the treatment of diseases annated with oxidation of lipids and proteins", CA 118:116773, (1993).

Mittal et al., *Proc. of National Academy of Science*, USA vol. 74, No. 10, pp. 4360–4364 (1977).

Palmer et al., *Nature*, vol. 327, pp. 524–526 (Jun. 11, 1987).

Parrett et al., *Journal of Pharmacology*, vol. 91, pp. 49–59 (1987).

*Physician's Desk Reference*, pp. 883, 977–978, 1782–1785, 1961 (1983).

Proctor et al., *Physiological Chemistry and Physics in Medical NMR*, vol. 16, pp. 175–195 (1984).

Ross, U.S. Department of Commerce, National Bureau of Standards, *Publication NSRDS–NBS59* (Jan. 1977).

Sekura, *Advances of Biology and Skin*, vol. XII, pp. 257–269, (1972).

Shapiro et al., *Journal of Clinical Endocrinology and Metabolism*, vol. 51, pp. 429–430 (1980).

Stewart, *International Journal of Dermatology*, vol. 17, pp. 167–179 (1978).

Thompson, *Federal Drug Administration Consumer*, pp. 10 and 12 (Mar. 10, 1981).

Tiffany–Castiglion, *Biochemical Pharmacology*, vol. 31, No. 2, pp. 181–188 (1982).

Torre (Ed.), *Annals of the New York Academy of Sciences*, vol. 411, Table of Contents (1983).

Vermorken, *Acta Dermatovener* (Stockholm), vol. 63, pp. 268–269 (1982).

Voorhees (Ed.), *Dermatologica*, vol. 175, suppl. 2, pp. 1–56 (1987).

Watanabe et al., *Archives of Dermatological Research*, vol. 278, pp. 470–473 (1986).

Weissmann, *Archives of Dermatology*, vol. 121, pp. 57–62 (1985).

Yoshioka et al., *Archives of Dermatological Research*, vol. 278, pp. 177–183 (1986).

Proctor, *Archives of Dermatology*, p. 1146 (Aug. 1989).

(List continued on next page.)

*Primary Examiner*—Deborah Lambkin
*Attorney, Agent, or Firm*—Daniel N. Lundeen; Sroufe, Payne & Lundeen, L.L.P.

[57] ABSTRACT

A composition and method for ameliorating a cellular dysfunction of a tissue such as the cosmetic treatment of hair loss and stimulation of hair growth are disclosed. The method comprises administering a nitroso or nitrone spin trap such as N-t-butyl-α-phenylnitrone (PBN) to the affected tissue.

17 Claims, No Drawings

OTHER PUBLICATIONS

Gelvan et al., *Proc. of National Academy of Science, USA*, vol. 88, pp. 4680–4684 (1991).
Carney et al., *Proc. of National Academy of Science, USA*, vol. 88, pp. 3633–3636 (1991).
Floyd, *Science*, vol. 254, p. 1597 (1991).
Anderson, *Chemical Abstracts*, vol. 90, pp. 311K (1979).
Ando et al., *Chemical Abstracts*, 93:79872n (1980).
Bazzano et al., *Journal of American Academy of Dermatology*, vol. 15, pp. 880–883 (1986).
Berry, *Pharmacology of the Skin*, vol. 1, pp. 121–137 (1987).
Cheng et al., *Archives of Dermatological Research*, vol. 278, pp. 470–473 (1986).
Cumming et al., *Journal of American Medical Association*, vol. 247, pp. 1295–1298 (1982).
*Current Therapy*, pp. 599–603 (1984).
Dahl, *Men's Fitness*, pp. 93–95 (Feb. 1989).
Dawber, *Dermatologica*, vol. 175, suppl. 2, pp. 23–28 (1987).
DeVillez, *Archives of Dermatology*, vol. 121, pp. 197–202, (1985).
*Dermatologica*, vol. 175, suppl. 2, pp. 1–56 (Oct. 87).
Dostert et al., *Xenobiotica*, vol. 15, No. 10, pp. 799–803 (1985).
Ehman et al., *Investigative Radiology*, vol. 21, pp. 125–131 (1986).
Feelisch et al., *Evr. Journal of Pharmacology*, vol. 139, pp. 19–30 (1987).
Feelisch et al., *Evr. Journal of Pharmacology*, vol. 142, pp. 405–409 (1987).
Fiedler, *Dermatologica*, vol. 175, suppl. 2, pp. 29–35 (1987).
Fox et al., *Annals of the New York Academy of Sciences*, vol. 411, pp. 14–19 (1983).
Goffman et al., *International Journal of Radiation, Oncology, Biology and Physics*, vol. 22, pp. 803–806 (Nov. 4, 1992).
Headington, *Current Therapeutic Research*, vol. 36, pp. 1098–1105 (1984).
Hearse et al., *Circulation Research*, vol. 60, pp. 375–383 (1987).
Herschler, *Chemical Abstracts*, vol. 78, pp. 115239 (1973).
Ignarro et al., *Biochemica et. Biophysica Acta*, vol. 631, pp. 221–231 (1980).
*J., Soc. Cosmetology Chem.*, (Italy) vol. 33, pp. 95–96 (Mar./Apr. 1982).
*Journal of American Medical Association*, vol. 260, No. 20 (1988).
Karlsson et al., *Journal of Cyclic Nucleotide and Protein Res.*, vol. 10, No. 4, pp. 309–315 (1985).
Kvedar, *Journal of American Academic Dermatology*, vol. 12, pp. 215–225 (1985).
*Longevity*, vol. 2, No. 3, p. 26 (Jan. 1988).
Lucky, *Archives of Dermatology*, vol. 121, pp. 57–62 (1985).
Messina, *Current Therapeutic Research*, vol. 34, pp. 319–324 (1983).
Messina, *Current Therapeutic Research*, vol. 38, pp. 269–282 (1985).
Mitchell et al., IBC USA Conference, South Natick, MA (Jun. 27, 1991).

TOPICAL SPIN TRAP COMPOSITION AND METHOD

CROSS-REFERENCE TO RELATED APPLICATIONS

This application is a continuation-in-part of applications Ser. No. 08/229,374, filed Apr. 18, 1994, now U.S. Pat. No. 5,470,876, and Ser. No. 08/193,228, filed Feb. 7, 1994, now U.S. Pat. No. 5,472,687, which are continuations-in-part of Ser. No. 08/021,970, filed Feb. 24, 1993, now U.S. Pat. No. 5,352,442; which is a continuation-in-part of Ser. No. 07/149,720, filed Jan. 29, 1988, abandoned; which is a continuation-in-part of application Ser. No. 07/008,186, filed Jan. 28, 1987, abandoned; which is a continuation-in-part of application Ser. No. 06/858,050, Apr. 30, 1986, abandoned; which is a continuation-in-part of application Ser. No. 06/757,131, Jul. 18, 1985, abandoned.

FIELD OF THE INVENTION

This invention relates to topical nitrone and nitroso spin traps such as N-t-butyl-α-phenylnitrone (PBN) and a method for treating hair loss therewith.

BACKGROUND OF THE INVENTION

Several compounds have recently gained recognition for ameliorating cellular dysfunction. One type of dysfunction which has been well studied is alopecia for which anti-alopecia agents such as minoxidil and cyoctol have gained attention. However, most of these anti-alopecia agents are only minimally effective in some cases and/or can cause adverse dermatological or systemic reactions. Thus, the search continues for new, safer and more effective anti-alopecia agents as well as agents useful for treating other dysfunctionalities.

SUMMARY OF THE INVENTION

Applicant has discovered that nitrone and nitroso spin traps have properties in the body for ameliorating cellular dysfunction in tissue attributed, in part, to high energy oxygen and hydroxyl free radicals, and enhancing recuperation of the tissue. N-t-butyl-α-phenylnitrone (PBN) can be administered, for example, as an anti-alopecia agent to stimulate cosmetic hair growth, or as a protectant against ischemia-reperfusion-mediated injury to the heart and brain.

DETAILED DESCRIPTION OF THE INVENTION

In the present invention, a nitrone and/or nitroso spin trap is compounded in a pharmaceutical formulation or carrier for topical or internal administration. The topical pharmaceutical carrier in which the spin trap compound is generally substantially homogeneously dispersed can be an aqueous dispersion or suspension, or a water-in-oil or oil-in-water emulsion depending on the administration route. Topical pharmaceutical carriers which can be mentioned include water, urea, alcohols and glycols such as methanol, ethanol, propanol, butanol, ethylene glycol, propylene glycol, and the like. Internally administered pharmaceutical carriers typically include a sterile vehicle such as water or ethanol in which the spin trap compound is suspended, dispersed or dissolved.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

Nitrone and nitroso spin trap compounds are commercially available. Exemplary nitrone and nitroso spin trap compounds include N-t-butyl-α-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α-(4-pyridyl-1-oxide)-N-t-butylnitrone, 3,3,5,5-tetramethylpyrroline N-oxide, 2,4,6-tri-t-butylnitrosobenzene, and the like. For purposes of clarity and illustration, reference is made below to N-t-butyl-α-phenylnitrone (PBN) by way of example and not limitation.

Effective amounts of the spin trap generally range from about 0.01 to about 20% by weight of the administered composition, more preferably from about 0.1 to about 10% by weight, most preferably from about 0.5 to about 3% by weight, but more or less can be present in the composition depending on the particular spin trap formulation and the treatment conditions.

The spin trap can be used alone or in combination with other additaments which are available to enhance the function of hair growth stimulation such as, for example, the hydroxyl radical scavengers, antiandrogens and others described in International Publication No. WO 87/00427 (International Application No. PCT/US86/01393) published on Jan. 29, 1987; and European Patent Application No. 89300785.6, Publication No. 0327263/A1, published Aug. 9, 1989; both of which are hereby incorporated in their entirety herein as though fully set forth verbatim, including Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the PBN can be administered to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topically applied PBN is not limited thereto, however, and the stimulation of hair growth can include an increased rate of growth, increased hair diameter, follicular neogenesis, and the like; inhibiting hair loss or alopecia from progressing, for example, in male pattern baldness, or during the course of treatment with other therapeutic agents known to induce hair loss, such as chemotherapy or radiation therapy in cancer treatment. PBN can also be useful by topical, oral or parental administration in ameliorating the rate of protein oxidation, DNA scission, cell viability loss, and the like in the tissue of internal organs such as the heart and brain; and ameliorating capillary loss, tissue atrophy characterized by a decrease in collagen and/or elastin and a decreased number, size and reproduction potential of fibroblasts, and strengthening the dermal-epidermal junction in skin; ischemic reperfusion injury secondary to myocardial infarction, stroke and surgical procedures; wound healing, for example, in burns and diabetic ulcerations; inflammatory and degenerative diseases such as rheumatoid arthritis, lupus and the like; fibrotic diseases such as Peyronie's disease, scarring, pulmonary fibrosis, and vitreous fibrosis; prevention of free-radical-induced vascular damage such as in atherosclerosis; other free radical diseases as outlined in Proctor et al., "Free Radicals and Disease in Man," *Physiological Chemistry and Physics and Medical NMR*, volume 16, pp. 175–195 (1984) which is hereby incorporated herein by reference; and the like.

The invention is illustrated by way of the following examples:

EXAMPLE 1

A PBN shampoo is prepared by mixing 0.5 g of PBN in 500 ml of a commercially available shampoo. The shampoo is used daily on the scalp for normal shampooing of the hair for a period of from 3 to 6 months to obtain cosmetic hair growth.

EXAMPLE 2

A solution of PBN is prepared and used in the course of radiation treatment. PBN, obtained commercially from Aldrich Chemical Company, is dissolved in 70 percent ethanol/ 30 percent water at a concentration of 70 mg/ml. Topical application of the solution is made prior to irradiation exposure at 20Gy to 50Gy. Hair loss in the treated PBN subjects is less severe and returns to normal more rapidly than in the control group similarly treated with the same ethanol/water solution without PBN. Skin samples obtained from the treated group test positive for the presence of PBN, while other tissue and blood specimens generally test negative. The application of the solution can also continue daily after the irradiation exposure. See Goffman, et al., "Topical Application of Nitroxide Protects Radiation-Induced Alopecia in Guinea Pigs," International Journal of Radiation Oncology, Biology and Physics, Volume 22, pp. 803–806, 1992, which is hereby incorporated herein by reference.

EXAMPLE 3

A 0.4 or 1 mM solution of PBN is used to significantly reduce cardiac injury caused by reperfusion arrhythmia-ventricular fibrillation and ventricular tachycardia, as well as, post ischemic release of lactate dehydrogenase and OH • formation in isolated rat hearts subjected to regional ischemia. The rat hearts are obtained and perfused using a modified Krebs-Henseleit (KH) buffer, as detailed in Gelvan et al., "Cardiac Reperfusion Damage Prevented by a Nitroxide Free Radical," *Proceedings of the National Academy, of Sciences*, USA, Medical Sciences, Vol. 88, pp. 4680–4684, June 1991, which is hereby incorporated herein by reference, in which a TEMPO solution was added to the perfusate. After reperfusion, heart function and resulting damage is analyzed. PBN is found to strongly protect against reperfusion injury by preventing OH-formation rather than by decreasing heart rate or by direct suppression of arrhythmia.

EXAMPLE 4

Male gerbils, retired breeders 15–18 months of age, are treated with intraperitoneal injections of PBN in saline twice daily at 32 mg/kg for 14 days as described in Carney et al., "Reversal of age-related increase in brain protein oxidation, decrease in enzyme activity, and loss in temporal and spatial memory by chronic administration of the spin-trapping compound n-tert-t-butyl-α-phenylnitrone, " *Proc. Nat'l. Acad. Sci. USA*, vol. 88, pp. 3633–3636 (May 1991) which is hereby incorporated by reference. The PBN administration decreases the amount of oxidized protein and number of errors made in a radial-arm maze, and increases the glutamine synthetase and neutral protease activity in brain. These chemical and behavioral parameters are restored to about the same values observed in placebo-treated mail gerbils of about 3 months of age.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

I claim:

1. A method for reducing the amount of oxygen and hydroxyl free radicalism tissue of an organism comprising the step of:

administering a nitrone or nitroso spin trap to the tissue in an amount effective to inhibit the free radicals, wherein the spin trap is selected from N-t-butyl-α-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α-(4-pyridyl-1-oxide)-N-t-butylnitrone, 3,3,5,5-tetramethylpyrroline N-oxide, and 2,4,6-tri-t-butylnitrosobenzene.

2. The method of claim 1, wherein the administration is topical.

3. The method of claim 2, wherein the spin trap is in the form of a dispersion, suspension or emulsion selected from creams, lotions, shampoos and cream rinses.

4. The method of claim 3, wherein the spin trap is present in a pharmaceutical carrier in an amount effective to stimulate hair growth.

5. The method of claim 3, wherein the dispersion, suspension or emulsion comprises from about 0.01 to about 20 percent by weight of said nitrone or nitroso spin trap.

6. The method of claim 1, wherein the spin trap comprises, N-t-butyl-α-phenylinitrone.

7. A method for treating hair loss, comprising the step of:

administering an effective amount of a spin trap selected from N-t-butyl-α-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α-(4-pyridyl-1-oxide)-N-t-butylnitrone, 3,3,5,5-tetramethylpyrroline N-oxide, and 2,4,6-tri-t-butylnitrosobenzene to the affected area.

8. The method of claim 7, wherein the administration step is topical.

9. The method of claim 8, wherein the spin trap is in the form of a dispersion, suspension or emulsion selected from creams, lotions, shampoos and cream rinses.

10. The method of claim 7, wherein the spin trap comprises N-t-butyl-α-phenylinitrone.

11. The method of claim 9, wherein the dispersion, suspension or emulsion comprises from about 0.01 to about 20 percent by weight of said spin trap.

12. A topical hair loss treatment composition comprising a nitroso or nitrone spin trap in association with a topical pharmaceutical carrier comprising a water and oil emulsion.

13. The composition of claim 12, comprising from 0.01 to 20 weight percent of a spin trap selected from N-t-butyl-α-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α-(4-pyridyl-1-oxide)-N-t-butylnitrone, 3,3,5,5-tetramethylpyrroline N-oxide, and 2,4,6-tri-t-butylnitrosobenzene.

14. The composition of claim 13, wherein the spin trap includes N-t-butyl-α-phenylnitrone.

15. A topical hair loss treatment composition comprising a nitroso or nitrone spin trap in association with a topical pharmaceutical carrier selected from creams, lotions, shampoos and cream rinses.

16. The composition of claim 15, comprising from 0.01 to 20 weight percent of a spin trap selected from N-t-butyl-α-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, α-(4-pyridyl-1-oxide)-N-t-butylnitrone, 3,3,5,5-tetramethylpyrroline N-oxide, 2,4,6-tri-t-butylnitrosobenzene.

17. The composition of claim 16, wherein the spin trap includes N-t-butyl-α-phenylnitrone.

* * * * *

UNITED STATES PATENT AND TRADEMARK OFFICE
CERTIFICATE OF CORRECTION

PATENT NO. : 5,723,502
DATED : March 3, 1998
INVENTOR(S) : Peter H. Proctor

It is certified that error appears in the above-indentified patent and that said Letters Patent is hereby corrected as shown below:

Column 4, line 16, claim 1, line 2: the term "radicalism" should be --radicals in--.

Column 4, line 37, claim 6, line 2: the period immediately after the word "comprises" should be deleted.

Signed and Sealed this

Nineteenth Day of January, 1999

Attest:

Attesting Officer

*Acting Commissioner of Patents and Trademarks*